US010390563B2

(12) United States Patent
Hawes et al.

(10) Patent No.: US 10,390,563 B2
(45) Date of Patent: Aug. 27, 2019

(54) ELECTRONIC SMOKING ARTICLE

(71) Applicant: ALTRIA CLIENT SERVICES LLC., Richmond, VA (US)

(72) Inventors: Eric Hawes, Midlothian, VA (US); Barry S. Smith, Hopewell, VA (US)

(73) Assignee: ALTRIA CLIENT SERVICES LLC, Richmond, VA (US)

( * ) Notice: Subject to any disclaimer, the term of this patent is extended or adjusted under 35 U.S.C. 154(b) by 28 days.

(21) Appl. No.: 14/774,039

(22) PCT Filed: Mar. 21, 2014

(86) PCT No.: PCT/US2014/031458
§ 371 (c)(1),
(2) Date: Sep. 9, 2015

(87) PCT Pub. No.: WO2014/153515
PCT Pub. Date: Sep. 25, 2014

(65) Prior Publication Data
US 2016/0021931 A1    Jan. 28, 2016

Related U.S. Application Data

(60) Provisional application No. 61/804,294, filed on Mar. 22, 2013.

(51) Int. Cl.
*A24F 47/00* (2006.01)
*H05B 3/00* (2006.01)
(Continued)

(52) U.S. Cl.
CPC ......... *A24F 47/008* (2013.01); *A61M 11/006* (2014.02); *A61M 11/042* (2014.02);
(Continued)

(58) Field of Classification Search
CPC ....... A24F 47/008; H05B 3/0014; H05B 3/06; H05B 3/12; A61M 11/006; A61M 15/06
(Continued)

(56) References Cited

U.S. PATENT DOCUMENTS

| 4,810,172 A * | 3/1989 | Fiedler | F04B 43/10 |
| | | | 417/394 |
| 8,903,228 B2 * | 12/2014 | Goodman | F22B 1/282 |
| | | | 131/330 |

(Continued)

FOREIGN PATENT DOCUMENTS

| CA | 2857989 A1 | 6/2013 |
| CN | 1541577 A | 11/2004 |

(Continued)

OTHER PUBLICATIONS

Chinese Office Action dated Apr. 7, 2017 issued in corresponding Chinese Application No. 201480023026.6 (with translation).

(Continued)

*Primary Examiner* — Alexander Gilman
(74) *Attorney, Agent, or Firm* — Harness, Dickey & Pierce, P.L.C.

(57) ABSTRACT

An electronic smoking article is disclosed, which includes an outer housing extending in a longitudinal direction; a micro pump system configured to pump a liquid material contained within a liquid supply reservoir through an outlet of the supply reservoir into a capillary; the capillary having an inlet and an outlet, the inlet in communication with the outlet of the liquid supply reservoir; a heating arrangement operable to heat the capillary to a temperature sufficient to at least initially volatilize the liquid material contained within the capillary; a power supply operable to apply voltage to the micro pump gas cell to generate a gas to drive the liquid material out of the liquid supply reservoir into the (Continued)

inlet of the capillary; at least one air inlet; and whereby air is mixed with the volatilized material to form an aerosol.

18 Claims, 3 Drawing Sheets

(51) Int. Cl.
| | |
|---|---|
| *H05B 3/06* | (2006.01) |
| *H05B 3/12* | (2006.01) |
| *H05B 3/42* | (2006.01) |
| *H05B 3/46* | (2006.01) |
| *F04B 19/00* | (2006.01) |
| *A61M 11/00* | (2006.01) |
| *A61M 15/06* | (2006.01) |
| *A61M 11/04* | (2006.01) |

(52) U.S. Cl.
CPC .......... *A61M 15/06* (2013.01); *F04B 19/006* (2013.01); *H05B 3/0014* (2013.01); *H05B 3/06* (2013.01); *H05B 3/12* (2013.01); *H05B 3/42* (2013.01); *H05B 3/46* (2013.01); *A61M 2205/3653* (2013.01); *A61M 2205/8206* (2013.01)

(58) Field of Classification Search
USPC ......................................................... 131/328
See application file for complete search history.

(56) References Cited

U.S. PATENT DOCUMENTS

| | | | | |
|---|---|---|---|---|
| 9,532,600 | B2 * | 1/2017 | Thorens | ................ A24F 47/008 |
| 9,560,883 | B2 * | 2/2017 | Hawes | ................ A24F 47/008 |
| 9,687,027 | B2 * | 6/2017 | Poston | ................ A24F 47/008 |
| 2002/0008122 | A1 * | 1/2002 | Ritsche | ............... B05B 11/0037 |
| | | | | 222/383.3 |
| 2004/0226568 | A1 * | 11/2004 | Takeuchi | ............... A24B 15/16 |
| | | | | 131/194 |
| 2006/0196518 | A1 | 9/2006 | Hon | |
| 2007/0131717 | A1 * | 6/2007 | Davies | ................ A61M 15/009 |
| | | | | 222/162 |
| 2008/0257915 | A1 * | 10/2008 | Wold | .................... B05B 11/025 |
| | | | | 222/389 |
| 2011/0094523 | A1 * | 4/2011 | Thorens | ................ A24F 47/008 |
| | | | | 131/194 |
| 2011/0290248 | A1 * | 12/2011 | Schennum | ............ A24F 47/002 |
| | | | | 128/202.21 |
| 2012/0090630 | A1 | 4/2012 | Hon | |
| 2012/0145742 | A1 | 6/2012 | Wold et al. | |
| 2012/0199146 | A1 * | 8/2012 | Marangos | ............. A24F 47/008 |
| | | | | 131/328 |
| 2012/0273589 | A1 | 11/2012 | Hon | |
| 2013/0026194 | A1 | 1/2013 | Wold et al. | |
| 2013/0199528 | A1 * | 8/2013 | Goodman | ................ F22B 1/282 |
| | | | | 128/203.26 |
| 2013/0276804 | A1 | 10/2013 | Hon | |
| 2014/0261492 | A1 * | 9/2014 | Kane | ..................... A24F 47/008 |
| | | | | 131/328 |
| 2016/0021931 | A1 * | 1/2016 | Hawes | .................. A24F 47/008 |
| | | | | 131/328 |

FOREIGN PATENT DOCUMENTS

| | | | | |
|---|---|---|---|---|
| EP | 1618803 | A1 * | 1/2006 | ........... A24F 47/002 |
| EP | 1618803 | A1 | 1/2006 | |
| EP | 2319334 | A1 | 5/2011 | |
| KZ | 11053 | B | 12/2001 | |
| KZ | 26638 | B | 12/2012 | |
| RU | 2268631 | C2 | 1/2006 | |
| WO | WO-9506314 | A1 | 3/1995 | |
| WO | WO-2010133334 | A1 | 11/2010 | |
| WO | WO-2011147687 | A1 | 12/2011 | |

OTHER PUBLICATIONS

International Search Report PCT/ISA/210 for International Application No. PCT/US2014/031458 dated Jul. 17, 2014.
Kazakhstan Office Action dated Dec. 8, 2016 issued in corresponding Kazakhstan Patent Application No. 2015-1213.1.
Office Action for corresponding Russian App. No. 2015145374 dated Sep. 12, 2017 and English translation.
Office Action for corresponding Chinese Application No. 201480023026.6 dated Jan. 30, 2018 and English translation thereof.
Office Action for corresponding European Application No. 14720017.4 dated Mar. 1, 2018.
Office Action for corresponding Ukrainian Application No. a201510251 dated Mar. 6, 2018 and English translation thereof.
Office Action dated Mar. 29, 2019 in corresponding Malaysian Patent Application No. PI-2015002409.
Office Action dated Apr. 17, 2019 in corresponding Chinese Application No. 201480023026.6.
European Patent Office Communication dated Oct. 19, 2018 issued in coresponding European Application No. 14720017.4.
Office Action for corresponding Chinese Application No. 201480023026.6 dated Oct. 24, 2018, and English translation thereof.

* cited by examiner

ELECTRONIC SMOKING ARTICLE

RELATED APPLICATION(S)

The present application claims priority under 35 U.S.C. 119 to U.S. Provisional Patent Application No. 61/804,294, filed on Mar. 22, 2013, the entire content of which is hereby incorporated by reference.

SUMMARY

The teachings herein provide embodiments of novel smoking articles such as electronic cigarettes, cigars and aerosol generators. These devices can include a capillary designed to deliver liquid material from a liquid reservoir to a heater. The disclosed devices can be activated by a consumer drawing on a mouth end of the smoking article to deliver an aerosol to the user. The teachings include application of a gas cell based micro pump as a fluid delivery device in an aerosol based smoke delivery device.

In accordance with an exemplary embodiment, an electronic smoking article is disclosed, the electronic smoking article comprising: an outer housing extending in a longitudinal direction; a micro pump system configured to pump a liquid material contained within a liquid supply reservoir through an outlet of the supply reservoir into a capillary; the capillary having an inlet and an outlet, the inlet in communication with the outlet of the liquid supply reservoir; a heating arrangement operable to heat the capillary to a temperature sufficient to at least initially volatilize the liquid material contained within the capillary; a power supply operable to apply voltage to the micro pump gas cell to generate a gas to drive the liquid material out of the liquid supply reservoir into the inlet of the capillary; at least one air inlet; and whereby air is mixed with the volatilized material to form an aerosol In accordance with another exemplary embodiment, an electronic smoking article is disclosed, the electronic smoking article comprising: a liquid supply reservoir containing a liquid material; and a micro pump system comprising: an expandable gas chamber comprising a moveable wall of the liquid supply reservoir; and a micro pump gas cell to generate a gas and to direct the gas to the expandable gas chamber to expand the expandable gas chamber, wherein expansion of the expandable gas chamber moves the wall to dispense the liquid material from the liquid supply reservoir.

In accordance with a further exemplary embodiment, a method of producing an aerosol from an electronic smoking article is disclosed, the method comprising: communicating liquid material to a capillary using a micro pump system to pump a liquid material from a liquid reservoir to an inlet of the capillary; and communicating electrical power from a power source to a heater operative upon the capillary, wherein the capillary discharges the liquid communicated to the capillary in an at least partially volatized condition into a mixing chamber to produce an aerosol.

In accordance with an exemplary embodiment, an aerosol generator is disclosed, the aerosol generator comprising: a heatable capillary; a source of liquid; and a micro pump gas cell operable to pump liquid from said source into said heatable capillary.

BRIEF DESCRIPTION OF THE DRAWINGS

The disclosure is explained below with reference to the exemplary embodiments shown in the drawings. In the drawings.

DETAILED DESCRIPTION

In accordance with an exemplary embodiment, an electronic smoking article, such as an electronic cigarette or electronic cigar, includes a micro pump system, which pushes a column of liquid material through a heatable capillary. In accordance with an exemplary embodiment, the micro pump system comprises a power source in the form of a battery and a micro pump gas cell that generates gas as it discharges to push a plunger or moveable structure, which drives the liquid material out a liquid reservoir at a constant flow rate into the capillary.

Figure 1:
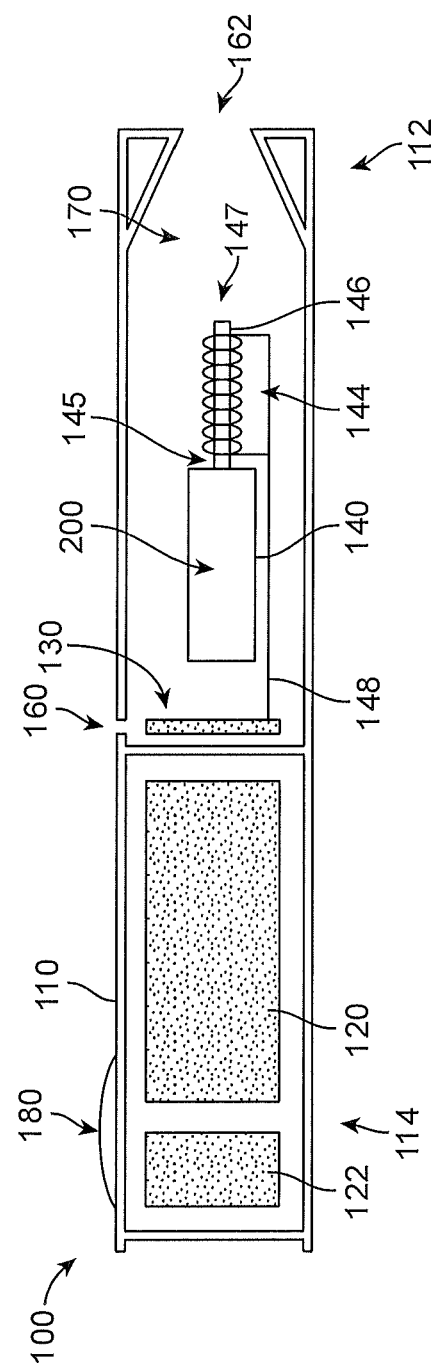
FIG. 1 is a cross-sectional view of an electronic smoking article in accordance with a first exemplary embodiment.

FIG. 1 shows an electronic cigarette 100 in accordance with an exemplary embodiment. As shown in FIG. 1, the electronic cigarette 100 includes a housing 110 having a mouth end 112 and a body end 114. In the body end 114, there is provided an electric power supply in the form of battery 120 and electric circuitry in the form of circuitry 122 and a puff detection system 130. In the mouth end 112, the cigarette 100 includes a cartridge 140, which houses a micro pump system 200, an electronically resistive heater 144, and a capillary 146. The micro pump system 200 delivers a liquid material 242 (FIG. 2) from a liquid supply reservoir (or fluid reservoir) 240 to the capillary 146, which is surrounded by the heater 144. In other embodiments, the heater 144 may comprise a portion of the capillary itself. In accordance with an exemplary embodiment, one end of the capillary 146 communicates with the liquid supply of the cartridge 140. The heater 144 is connected to the electric circuitry 122 via connections 148. The housing 110 also includes an air inlet 160, an air outlet 162 at the mouth end 112, and an aerosol forming chamber 170.

In use, the liquid material 242 is driven by the micro pump 200 from the fluid reservoir 240 into an inlet 145 of the capillary 146. When a user draws on the electronic cigarette 100 at the air outlet 162, ambient air is drawn through air inlet 160. In accordance with an exemplary embodiment, the electronic cigarette 100 can include a puff detection system 130, which senses the puff and activates the micro pump gas cell 210 (FIG. 2) and the heater 144. The battery 120 supplies a pulse of energy to the heater 144 to heat portions of the capillary 146 adjacent the heater 144. The liquid material 242 in the outlet end 147 of the capillary 146 is vaporized by the heater 144 to create a supersaturated vapor. At the same time, the liquid material 242 being vaporized is replaced by additional liquid material 242 moving along the capillary 146 by a pumping action from the micro pump system 200.

In accordance with an exemplary embodiment, the supersaturated vapor created is mixed with and carried in the air flow from the air inlet 160. In the aerosol forming chamber 170, the vapor condenses to form an inhalable aerosol, which is drawn through the outlet 162 of the article during a puff. As shown in FIG. 1, the circuitry 122 and the puff detection system 130 are preferably programmable. In accordance with an exemplary embodiment, the circuitry 122 and puff detection system 130 can be used to manage the operation of the electronic cigarette 100. In accordance with an exemplary embodiment, the micro pump system 200 in conjunction with the physical design of the electronic cigarette 100 can assist with control of the particle size in the aerosol.

The capillary 146 includes an inlet end 145 in fluid communication with the outlet 244 of the liquid supply reservoir 240 via a valve 230 (FIG. 2), and an outlet end 147 operable to expel volatilized liquid material from the capillary 146. In accordance with an exemplary embodiment, the capillary 146 has an internal diameter of about 0.01 to 10 mm, preferably 0.05 to 1 mm, and more preferably 0.05 to 0.4 mm. For example, the capillary 146 can have an internal diameter of about 0.05 mm. Alternatively, the capillary 146 can have an internal cross sectional area of $8\times10^{-5}$ to 80 $mm^2$, preferably 0.002 to 0.8 $mm^2$, and more preferably 0.002 to 0.05 $mm^2$. For example, the capillary 146 can have an internal cross sectional area of about 0.002 to 0.02 $mm^2$.

In accordance with an exemplary embodiment, the capillary 146 can have a length of about 5 mm to about 100 mm, more preferably about 10 mm to about 60 mm or about 20 mm to about 50 mm. For example, the capillary 146 can be about 50 mm in length and arranged such that a downstream, about 40 mm long portion of the capillary 146 forms a heated section and an upstream, about 10 mm long portion of the capillary 146 remains relatively unheated when the heater 144 is activated. In accordance with an exemplary embodiment, the capillary 146 has an internal diameter of about 0.17 mm to about 0.21 mm, an outer diameter of about 0.23 mm to about 0.25 mm and a length of about 5 mm to about 100 mm, for example, a length of about 50 mm. In an exemplary embodiment, the capillary 146 is substantially straight, coiled and/or includes one or more bends therein to conserve space.

In an exemplary embodiment, the capillary 146 is formed of a conductive material, and thus acts as its own heater. The capillary 146 may be any electrically conductive material capable of being resistively heated, while retaining the necessary structural integrity at the operating temperatures experienced by the capillary 146, and which is non-reactive with the liquid material. Suitable materials for forming the capillary 146 are selected from the group consisting of stainless steel, copper, copper alloys, porous ceramic materials coated with film resistive material, Inconel® available from Special Metals Corporation, which is a nickel-chromium alloy, Nichrome, which is also a nickel-chromium alloy (including Nichrome), and combinations thereof.

In an exemplary embodiment, the capillary 146 is a stainless steel capillary 146, which serves as a heater via electrical connection 148 attached thereto for passage of direct or alternating current along a length of the capillary 146. Thus, the stainless steel capillary 146 is heated by resistance heating. The stainless steel capillary 146 is preferably circular in cross section. The capillary 146 may be of tubing suitable for use as a hypodermic needle of various gauges. For example, the capillary 146 may comprise a 32 gauge needle has an internal diameter of 0.11 mm and a 26 gauge needle has an internal diameter of 0.26 mm.

In an exemplary embodiment, the capillary 146 may be a non-metallic tube such as, for example, a glass tube. In such an exemplary embodiment, the heater 144 can be formed of a conductive material capable of being resistively heated, such as, for example, stainless steel, Nichrome or platinum wire, arranged along the glass tube. When the heater arranged along the glass tube is heated, liquid material in the capillary 146 can be heated to a temperature sufficient to at least partially volatilize liquid material in the capillary 146.

Figure 3:
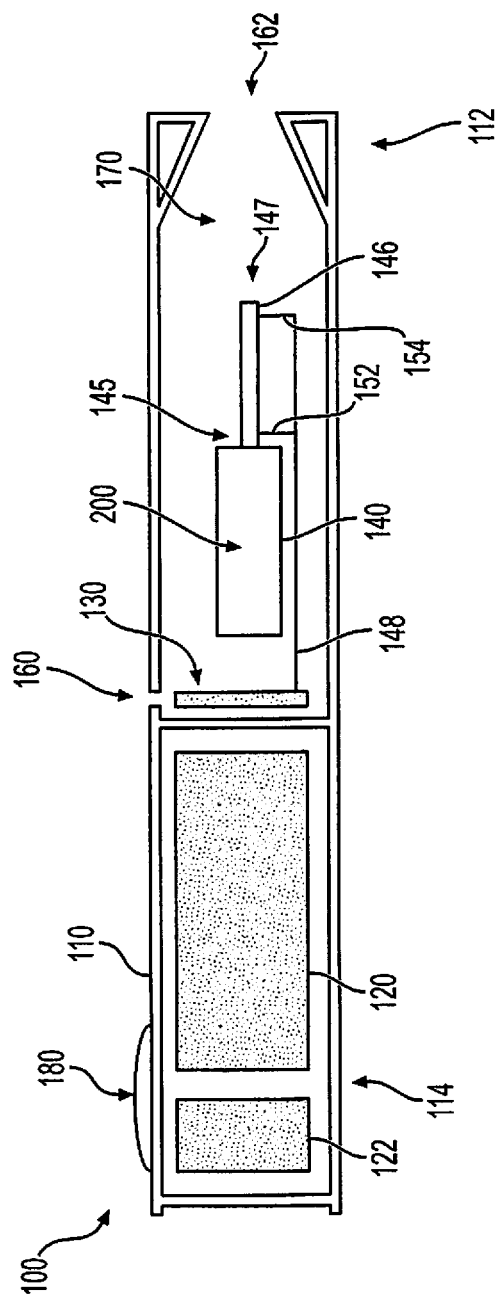
FIG. 3 is a cross-sectional view of an electronic smoking article in accordance with a second exemplary embodiment.

In accordance with an exemplary embodiment, the electrical connection 148 can be at least two spaced apart electrical connections, which are bonded to the metallic capillary 146. In the exemplary embodiment (and the embodiment of FIG. 3), the at least two electrical connections are brazed to the capillary 146. Preferably, one electrical lead 152 (see FIG. 3) is brazed to a first, upstream portion of the capillary 146 and a second electrical lead 154 (see FIG. 3) is brazed to a downstream portion of the capillary 146.

In use, once the capillary 146 is heated, the liquid material contained within a heated portion of the capillary 146 is volatilized and ejected out of the outlet 147 where it expands and mixes with air and forms an aerosol in a mixing chamber 170. The electronic cigarette 100 also includes at least one air inlet 160 operable to deliver air to the mixing chamber 170. Preferably, the air inlets 160 to the mixing chamber 170 are arranged downstream of the capillary 146 so as to minimize drawing air along the capillary and thereby avoid cooling of the capillary 146 during heating cycles. In use, the volatilized material expands out of the tube 146 and into the mixing chamber 170 where the volatized material can mix with air to form an aerosol, which is then drawn through the mouth end 112. In the exemplary embodiment, the at least one air inlet 160 includes one or two air inlets 160. Alternatively, the air inlets 160 can be three, four, or five or more. In accordance with an exemplary embodiment, the size and number of air inlets 160 can also aid in establishing the resistance to draw of the electronic cigarette 100.

The battery 120 can be a Lithium-ion battery or one of its variants, for example a Lithium-ion polymer battery. Alternatively, the battery 120 may be a Nickel-metal hydride battery, a Nickel cadmium battery, a Lithium-manganese battery, a Lithium-cobalt battery or a fuel cell. In accordance with an exemplary embodiment, the electronic cigarette 100 is usable by a smoker until the energy in the power supply is depleted. Alternatively, the battery 120 may be rechargeable and include circuitry (not shown) allowing the battery to be chargeable by an external charging device. For example, the circuitry, when charged, provides power for a pre-determined number of puffs, after which the circuitry must be re-connected to an external charging device.

The electronic cigarette 100 also includes control circuitry 122, which can be on a printed circuit board. Once a switch 180 is pressed, the power supply is activated and supplies power to the micro pump system 200 and the heater 144. The control circuitry 122 can also include a heater activation light (not shown) operable to glow when the heater 144 is activated. The control circuitry 122 can also include a timer operable to limit the time for which power is supplied to the micro pump system 200 and the heater 144. The time-period of the electric current supply to the the micro pump system 200 and the heater 144 may be pre-set depending on the amount of liquid desired to be vaporized. For example, the control circuitry 122 can be programmable for this purpose.

In accordance with an exemplary embodiment, when activated, the heater 144 heats a portion of the capillary 146 for less than about 10 seconds, more preferably less than about 7 seconds. Thus, the power cycle (or maximum puff length) can range in period from about 1 second to about 10 seconds.

FIG. 2 is a cross-sectional view of a portion of an electronic cigarette 100 having a micro pump system 200 and a capillary 146 in accordance with an exemplary embodiment. The micro pump system 200 can include a micro pump gas cell 210, a plunger 220, a valve 230, and a liquid supply reservoir 240. As shown in FIG. 2, the electronic cigarette 100 includes an outer cylindrical housing 110 extending in a longitudinal direction. The micro pump system 200 is configured to pump a liquid material 242 from a liquid supply reservoir 240 through an outlet 244 into an inlet 145 of the capillary 146. In accordance with an exemplary embodiment, the liquid supply reservoir 240 comprises a liquid material 242, which is volatilized when heated and forms an aerosol when discharged from the capillary 146.

In accordance with an exemplary embodiment, a power supply in the form of a battery 120 is operable to apply voltage across to a heater 144 operable to heat the capillary 146 to a temperature sufficient to at least initially volatilize liquid material 242 contained within the capillary 146. The battery 120 is also operable to apply voltage to the micro pump gas cell 210 to generate a gas 212. The pressure of the generated gas 212 moves the plunger 220 along a forward direction in a linear path within the micro pump system 200 to pump the liquid material 242 out of the liquid supply reservoir 240. In lieu or in addition to the plunger 220, the reservoir may include a flexible bladder, in which case the out of the micro-pump gas cell 210 would compress the bladder to pump fluid from the reservoir.

In accordance with an exemplary embodiment, the micro pump gas cell 210 forms a first wall of an expandable gas chamber 214 and the moveable plunger 220 forms a second wall of the expandable gas chamber 214. The plunger 220 also forms a moveable wall of the fluid reservoir 240. In use, the micro pump gas cell generates a gas 212 on demand and directs the gas 212 into the expandable gas chamber 214 to expand the expandable gas chamber 214, wherein expansion of the expandable gas chamber 214 moves the plunger 220 in a forward direction along a linear path to reduce a volume of the fluid reservoir 240, which dispenses or pushes the liquid material 242 from the fluid reservoir 240 into the inlet 145 of the capillary 146.

Figure 2:
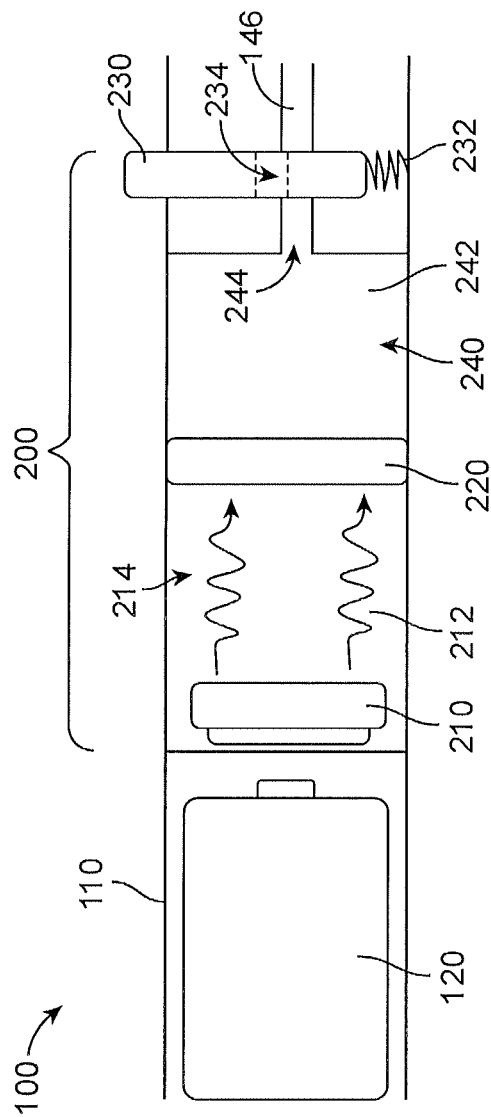
FIG. 2 is a cross-sectional view of a portion of an electronic smoking article having a micro pump system and a capillary in accordance with an exemplary embodiment.

As shown in FIG. 2, the liquid supply reservoir 240 can be an elongated body having an outlet 244, which is in fluid communication with a valve 230. The valve 230 inhibits flow back of liquid material 242 into the liquid supply reservoir 240. In accordance with an exemplary embodiment, the valve 230 can be a spring-biased valve 232 having an opening 234, which allows the flow of liquid material 242 from the liquid reservoir 240 into the inlet of the capillary 146. Simultaneously, to delivering liquid material 242 to the capillary 146, the power supply 120 is activated and the capillary 146 is heated to form a heated section wherein the liquid material 242 is volatilized. Upon discharge from the heated capillary 146, the volatilized material expands, mixes with air and forms an aerosol.

In accordance with an exemplary embodiment, the liquid material 242 includes a tobacco-containing material including volatile tobacco flavor compounds which are released from the liquid upon heating. The liquid material 242 may also be a tobacco flavor containing material or a nicotine-containing material. Alternatively, or in addition, the liquid material 242 may include a non-tobacco material. For example, the liquid material 242 may include water, solvents, ethanol, plant extracts and natural or artificial flavors. Preferably, the liquid material further includes an aerosol former. Examples of suitable aerosol formers are glycerine and propylene glycol.

In an exemplary embodiment, the electronic cigarette 100 is about the same size as a conventional cigarette. In some embodiments, the electronic cigarette 100 can be about 80 mm to about 88 mm long and about 7 mm to about 8 mm in diameter. For example, in an exemplary embodiment, the electronic cigarette 100 is about 84 mm long and has a diameter of about 7.8 mm.

The outer cylindrical housing 110 of the electronic cigarette 100 may be formed of any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK), ceramic, and polyethylene.

In an exemplary embodiment, the volatilized material formed as described herein can at least partially condense to form an aerosol including particles. The particles contained in the vapor and/or aerosol can range in size from about 0.5 micron to about 4 microns, for example, about 1 micron to about 4 microns. In an exemplary embodiment, the vapor and/or aerosol has a particle size of about 3.3 microns or less. In addition, the particles can be substantially uniform throughout the vapor and/or aerosol.

The heater 144 preferably includes an electrical heating element. The heater 144 preferably includes an electrically resistive material. Suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may include doped or undoped ceramics.

Examples of suitable doped ceramics include doped silicon carbides. Examples of suitable metals include titanium, zirconium, tantalum and metals from the platinum group. Examples of suitable metal alloys include stainless steel, Constantan, nickel-, cobalt-, chromium-, aluminum-titanium-zirconium-, hafnium-, niobium-, molybdenum-, tantalum-, tungsten-, tin-, gallium-, manganese- and iron-containing alloys, and super-alloys based on nickel, iron, cobalt, stainless steel, Timetal® and iron-manganese-aluminum based alloys. Timetal® is a registered trademark of Titanium Metals Corporation, 1999 Broadway Suite 4300, Denver, Colo. In composite materials, the electrically resistive material may optionally be embedded in, encapsulated or coated with an insulating material or vice-versa, depending on the kinetics of energy transfer and the external physicochemical properties required.

The heater 144 may take any suitable form. For example, the heater 144 may take the form of a heating blade. Alternatively, the heater 144 may take the form of a casing or substrate having different electro-conductive portions, or an electrically resistive metallic tube. Alternatively, the heater 144 may be a disk (end) heater or a combination of a disk heater with heating needles or rods. Alternatively, the heater 144 may take the form of a metallic etched foil insulated between two layers of an inert material. In that case, the inert material may include Kapton, all-polyimide or mica foil. Alternatively, the heater 144 may take the form of a sheet of material, which may be rolled around at least a portion of the capillary 146. Alternatively, the heater 144 may take the form of an etched foil folded around at least a portion of the capillary. The etched foil may include a metal sheet cut by a laser or by electro-chemical process. The sheet may be made from any suitable material, for example, an iron-aluminum based alloy, an iron-manganese-aluminum base alloy or Timetal®. The sheet may be rectangular in shape, or may have a patterned shape, which may form a coil-like structure when rolled around the capillary. Other alternatives include a heating wire or filament, for example a nickel-chromium (Ni—Cr), platinum, tungsten or alloy wire.

In an exemplary embodiment, the heater 144 includes a coil of wire at least partially surrounding the capillary 146. In an exemplary embodiment, the heater 144 is a metal wire and/or a metal alloy wire. The heater 144 can be a coil, which can extend fully or partially along the length of the capillary 146. The coil may extend fully or partially around the circumference of the capillary 146. In another embodiment, the coil is not in contact with the capillary 146, which allows the heating coil to heat the capillary 146 but reduces wastage by not vaporizing more liquid than necessary. This also reduces the amount of liquid which condenses on the inside walls, thereby reducing cleaning requirements.

The electronic cigarette 100 can include a puff indicator (not shown) for indicating when the heater 144 is activated. In the embodiment in which the electric circuitry includes a puff sensor, the indicator may be activated when the sensor senses air flow indicative of the user taking a puff. In the embodiment in which the electric circuitry includes a manually operable switch, the indicator may be activated by the switch.

In accordance with an exemplary embodiment, the electronic cigarette 100 having a micro pump system 200 as shown in FIGS. 1-2 can be configured to deliver a fluid material 242 at a constant flow rate of about 1 to 5 microliters/second, when the valve 230 is open (if a valve 230 is used). In accordance with an exemplary embodiment, the micro pump system 200 is configured to displace a total of about 0.5 to 2.0 milliliters of a liquid material 242 during a life of the system with cycle to cycle consistency. For example, the electronic cigarette 100 having a micro pump system 200 can have a life of about 250 cycles, with a cycle duration of up to about 5 seconds and a time between cycles of about 1 second or greater. In accordance with an exemplary embodiment, an outer diameter of the micro pump system 200 can be correlated based on capacity and size, for example, less than 8 mm for an exemplary embodiment. In addition, the micro pump system 200 is preferably isolated from the liquid material 242 and external environment. Further details of suitable gas-cell micro-pumps are provided in U.S. Pat. Nos. 8,113,390 and 8,353,426, which are incorporated herein by reference in their entireties.

The teachings herein are applicable to all forms of electronic smoking articles, such as electronic cigarettes, cigars, pipes, hookahs and others, regardless of their size and shape.

When the word "about" is used in this specification in connection with a numerical value, it is intended that the associated numerical value include a tolerance of ±10% around the stated numerical value.

Moreover, when the words "generally" and "substantially" are used in connection with geometric shapes, it is intended that precision of the geometric shape is not required but that latitude for the shape is within the scope of the disclosure. When used with geometric terms, the words "generally" and "substantially" are intended to encompass not only features, which meet the strict definitions but also features, which fairly approximate the strict definitions.

It will now be apparent that a new, improved, and non-obvious electronic cigarette has been described in this specification with sufficient particularity as to be understood by one of ordinary skill in the art. Moreover, it will be apparent to those skilled in the art that numerous modifications, variations, substitutions, and equivalents exist for features of the electronic cigarette, which do not materially depart from the spirit and scope of the invention. Accordingly, it is expressly intended that all such modifications, variations, substitutions, and equivalents which fall within the spirit and scope of the invention as defined by the appended claims shall be embraced by the appended claims.

What is claimed is:

1. An electronic vaping article, the electronic vaping article comprising:
   an outer housing extending in a longitudinal direction;
   a micro pump system configured to pump a liquid material contained within a liquid supply reservoir through an outlet of the liquid supply reservoir into a capillary, the capillary having an inlet and an outlet, the inlet in communication with the outlet of the liquid supply reservoir;
   a first electrical lead and a second electrical lead each connected to the capillary, the capillary configured to increase in heat to a temperature sufficient to at least initially volatilize the liquid material pumped into the capillary;
   a power supply configured to apply voltage to the micro pump system to generate a gas to pump the liquid material out of the liquid supply reservoir into the inlet of the capillary and further configured to supply power to the capillary via an electrical connection between the first electrical lead and the second electrical lead;
   at least one air inlet;
   a mixing chamber configured to receive air from the air inlet and further configured to receive the at least initially volatized liquid material from the capillary to mix with the air; and
   a valve between the outlet of the liquid supply reservoir and the inlet of the capillary.

2. The electronic vaping article of claim 1, further comprising:
   a mouth-end having at least one outlet, wherein the mouth-end is in fluid communication with the mixing chamber.

3. The electronic vaping article of claim 1, wherein the micro pump system comprises:
   an expandable gas chamber comprising a plunger forming a wall of the expandable gas chamber and moving along a linear path, and the plunger forming a wall of the liquid supply reservoir; and
   a micro pump gas cell configured to generate the gas and to provide the gas to the expandable gas chamber to cause expansion of the expandable gas chamber, and cause the plunger to move in a forward direction along the linear path to reduce a volume of the liquid supply reservoir to pump the liquid material from the liquid supply reservoir into the inlet of the capillary.

4. The electronic vaping article of claim 3, further comprising:
   a switch coupled to the power supply, the switch configured to activate the micro pump gas cell, and the micro pump gas cell being configured to deliver a constant flow rate of liquid material at about 0.5 microliters/second to 2.0 microliters/second when the valve is open.

5. The electronic vaping article of claim 1, wherein the capillary has an internal diameter of about 0.17 mm to about 0.21 mm, and a length of about 5 mm to about 100 mm.

6. The electronic vaping article of claim 1, wherein the capillary comprises a stainless steel tube or a non-metallic tube.

7. The electronic vaping article of claim 1, wherein the power supply includes a battery.

8. The electronic vaping article of claim 7, further comprising:
   a heating arrangement including a heater connected to the battery by the first electrical lead and the second electrical lead.

9. The electronic vaping article of claim 8, further comprising
   control circuitry configured to control supply of power to the heater.

10. The electronic vaping article of claim 1, wherein the at least one air inlet is located upstream of the capillary.

11. The electronic vaping article of claim 1, further comprising:
   a switch operative at an outer wall of the electronic vaping article and wherein pressure applied to the switch simultaneously activates the first electrical lead, the second electrical lead and micro pump system so as to release liquid material from the liquid supply reservoir into the capillary.

12. An electronic vaping article, the electronic vaping article comprising:
   a liquid supply reservoir containing a liquid material;
   a capillary in communication with an outlet of the liquid supply reservoir;
   a first electrical lead and a second electrical lead each connected to the capillary, the first and second electrical leads configured to apply a voltage across at least a portion of the capillary via an electrical connection between the first electrical lead and the second electrical lead with the capillary;
   a valve between the outlet of the liquid supply reservoir and an inlet of the capillary, configured to limit a flow of liquid material back into the liquid supply reservoir;
   a mixing chamber configured to receive air and further configured to receive at least initially volatized liquid material from the capillary to mix with the air; and
   a micro pump system comprising:
      an expandable gas chamber comprising a moveable wall of the liquid supply reservoir; and
      a micro pump gas cell to generate a gas and to provide the gas to the expandable gas chamber to expand the expandable gas chamber, wherein expansion of the expandable gas chamber moves the moveable wall to dispense the liquid material from the liquid supply reservoir.

13. The electronic vaping article of claim 12, further comprising:
   a power source connected to the micro pump gas cell.

14. The electronic vaping article of claim 13, further comprising:
   a switch coupled to the power source, the switch configured to activate the micro pump gas cell, wherein the micro pump gas cell being configured to deliver a constant flow rate of liquid material at about 0.5 microliters/ second to 2.0 microliters/second when the valve is open.

15. A method of producing an aerosol from an electronic vaping article, the method comprising:
   communicating liquid material to a capillary using a micro pump system to pump a liquid material from a liquid supply reservoir to an inlet of the capillary;
   causing a valve to actuate, the valve being at an inlet of the capillary; and
   connecting, electrically, electrical power from a power source to the capillary,
   wherein the capillary discharges the liquid material communicated to the capillary in an at least partially volatized condition into a mixing chamber to mix with air and produce an aerosol.

16. The method of claim 15, further comprising:
   generating a gas with a micro pump gas cell; and
   communicating the generated gas with the liquid supply reservoir to dispense the liquid material from the liquid reservoir into the inlet of the capillary.

17. The method of claim 16, further comprising:
   limiting a flow of liquid material back into the liquid reservoir by closing the valve.

18. An aerosol generator, the aerosol generator comprising:
   a heatable capillary configured to increase in heat via application of a voltage, from a power source electrically connected to the capillary, across at least a portion of the capillary;
   a valve at an inlet to the heatable capillary;
   a source of liquid;
   a micro pump gas cell operable to pump liquid from said source of liquid into said heatable capillary; and
   a mixing chamber configured to receive air and further configured to receive at least initially volatized liquid material from the heatable capillary to mix with the air.

* * * * *